(12) United States Patent
Van Dalen et al.

(10) Patent No.: US 8,857,991 B2
(45) Date of Patent: Oct. 14, 2014

(54) METHOD AND APPARATUS FOR DETERMINING OCULAR MOTOR FUNCTION

(76) Inventors: Johan T. W. Van Dalen, Tucson, AZ (US); Dan D. Carda, Tucson, AZ (US)

( * ) Notice: Subject to any disclaimer, the term of this patent is extended or adjusted under 35 U.S.C. 154(b) by 403 days.

(21) Appl. No.: 13/094,760

(22) Filed: Apr. 26, 2011

(65) Prior Publication Data

US 2011/0199574 A1    Aug. 18, 2011

Related U.S. Application Data

(63) Continuation-in-part of application No. 12/563,957, filed on Sep. 21, 2009, now Pat. No. 8,491,123.

(51) Int. Cl.
*A61B 3/02*    (2006.01)
*A61B 3/08*    (2006.01)

(52) U.S. Cl.
CPC ..................................... *A61B 3/085* (2013.01)
USPC .......................................... 351/240; 351/244

(58) Field of Classification Search
USPC ......... 351/200, 205, 206, 221, 222, 240, 243, 351/245
See application file for complete search history.

(56) References Cited

U.S. PATENT DOCUMENTS

| 5,241,332 A | 8/1993 | Farrell |
| 2009/0219482 A1* | 9/2009 | Van Dalen et al. ........... 351/201 |
| 2011/0261211 A1 | 10/2011 | Lee et al. |

* cited by examiner

*Primary Examiner* — Thomas K Pham
*Assistant Examiner* — Brandi Thomas
(74) *Attorney, Agent, or Firm* — Dale F. Regelman; Quarles & Brady LLP

(57) ABSTRACT

A method and an apparatus are presented for determining ocular motor function in a patient. The patient is instructed to wear a pair of test glasses comprising a first lens having a first color and a second lens having a second color, where the first color and the second color differ. A light comprising a first color is projected onto a vertical surface, where the location of the light can be moved on the vertical surface. For each value of (i), an (i)th fixation point is then projected on the vertical surface, where the (i)th fixation point is one of (N) total fixation points and comprises the second color. For each value of (i), a perceived location is recorded upon receiving a signal that the (i)th fixation point is illuminated by the light. Finally, the (N) perceived locations are transformed into an ocular motor function map.

6 Claims, 10 Drawing Sheets

METHOD AND APPARATUS FOR DETERMINING OCULAR MOTOR FUNCTION

CROSS REFERENCE TO RELATED APPLICATIONS

This Continuation-In-Part Application claims priority to a U.S. Non-Provisional Application having Ser. No. 12/563,957, which was filed on Sep. 21, 2009.

FIELD OF USE

The present invention relates generally to medical devices and more particularly to medical devices for determining ocular motor function.

BACKGROUND

Eye muscle dysfunction (strabismus) that affects horizontal movement of one or both eyes creates an inward or outward deviation, while disorders of the muscles that move the eyes up and down produce a vertical, and occasionally a rotational, ocular muscle imbalance. The ocular misalignment and accompanying double vision (diplopia) may result from direct or indirect damage to one or more of the cranial nerves (III, IV, VI) that innervate a particular extra-ocular muscle or muscle group (paralytic strabismus, as may occur following head trauma); as a consequence of direct involvement to the affected muscle itself (restrictive strabismus, for example in a patient with thyroid eye disease); or as a combination of the two etiologies (an orbital fracture where ocular contents, including muscles, are trapped in the fracture site, accompanied by an eye muscle paralysis of the trapped muscle). It is essential for eye care professionals to perform various tests that identify the involved muscle(s) and the type of deviation present, and quantify the amount of deviation for documentation purposes and to assist in planning a course of treatment.

Several methods exist to test for eye muscle dysfunction. One, the Hess test, utilizes a tangent screen consisting of a gray, wall-mounted board. A grid of coordinate curved horizontal and vertical lines appears as a virtual sphere. The patient is seated 0.5 meters from the screen with their head immobilized by a head/chin rest. Because the test is dependent upon color dissociation, the patient wears goggles of red and green complementary filters, red over the right eye and green over the left.

Another method, the Lancaster Red-Green test, is a variation of the Hess test and has similar components: it consists of a calibrated tangent screen, originally printed or sewn onto a piece of dark gray material. The nine diagnostic positions of gaze are marked on the screen, each 22.5 degrees or 45 prism diopters away from the center. The patient is seated 1 meter from the screen, and the head is similarly immobilized. The test utilizes the same goggles as the Hess test, but both the patient's and examiner's flashlights include a cover with a slit such that the light projected onto the screen is in the shape of a bar.

In older versions of the Hess screen the examiner holds a flashlight that projects a dot of red light onto the screen at the intersection of a coordinate. The patient, wearing the red-green goggles, holds a flashlight that projects a green linear target and subjectively superimposes it on the examiner's red dot. The examiner then moves the projected red dot until all nine (9) diagnostic positions of gaze have been evaluated. Newer electronic models have replaced the examiner's handheld flashlight and incorporated point red lights that randomly illuminate at each coordinate, allowing the examiner to observe the test procedure and document the patient's responses. The test is completed after the colored lenses are worn over each eye so that both right and left visual fields are plotted.

With the Lancaster Red-Green Test, both the red and green targets are linear, and again goggles of red and green complementary filters are worn by the patient, with the red filter worn over the right eye. An examiner must still be present to project one of the flashlights. The patient is asked to superimpose a green line projected from his flashlight onto a red line projected on the test screen from the examiner's flashlight. Again, the examiner moves the projected line of red light until all nine diagnostic positions of gaze have been evaluated. Horizontal, vertical, and torsional deviations can be identified and quantified after the patient's responses are correlated to the examiner's target placement. After the test is completed with the right eye fixating, the flashlights are exchanged and the test repeated so that the left eye assumes fixation.

Both the Hess and Lancaster Red-Green tests are fovea-to-fovea tests: the subjective visual direction of each fovea perceives the image seen through each colored filter, but is visually unaware of the image from the opposing eye. The test responses correspond to the direct projection of each fovea, and therefore correlate with the type of deviation present. A patient with a "crossed eye" (esotropia) will indicate that the images are crossed, while a patient who presents with an outward deviation of the eyes (exotropia), will perceive the images as uncrossed.

Since horizontal deviations are caused by problems affecting lateral movement of one or both eyes, these deviations are best appreciated if the green line from the patient's flashlight is projected so that a vertical line is created, while vertical deviations require the line to be projected in a horizontal fashion. While both the Hess and Lancaster Red-Green tests can be used to identify horizontal and vertical derivations, the presence of torsion, a rotational deviation where objects in the vertical meridian are seen as tilted, is difficult to assess with the Hess test because the two test objects—a dot of red light illuminated on the test screen and a line of green light projected from the flashlight held by the patient—are dissimilar in shape.

To score the Hess test, the examiner records the patient's responses on a paper chart, and then connects the dots, which form inner and outer grids. The inner grid measures deviations of approximately 15 degrees, or 30 prism diopters, the practical fields of eye movements from the primary position when the head is immobilized. The outer grid represents deviations of approximately 30 degrees or 60 prism diopters, when head movement is allowed to accompany the movements of the eyes.

The Lancaster Red-Green test also uses a grid for recording patient responses. A single grid sheet has two separate imprinted images of the test's tangent screen, one above the other, implying fixation with each eye. Responses are plotted on the top grid, as first the right eye fixates and then the bottom grid, for fixation with the left eye.

Once the dots are connected, the resulting grids from each test are interpreted by the examiner to reveal the etiology of the ocular misalignment. The grids from the Hess test implicate the affected eye (indicated by the smaller field), the associated under- and over-action of muscles, and may delineate a paralyzed muscle from a restricted one. With the Lancaster Red-Green test, the interpretation of the resulting grids and measurement of the deviation depends on the distance between the red and green lines, as well as the presence of horizontal, vertical or rotational separation of the lines. The field of greatest separation identifies the affected muscle(s) or the greater deviation created when the eye with a restriction fixates; the displaced direction of the patient's line—horizontal, vertical and/or rotational—indicates which horizontal and/or vertical muscles are involved.

While the Hess and Lancaster Red-Green tests aid in the detection of paretic extraocular muscle palsies and of strabismus, their use has been limited by the need for a physician or technician to record the results on an examination chart. Not only does this add to the cost of administering the test, but it introduces a source of error. Furthermore, while the Hess and Lancaster Red-Green tests use point sources or symmetric fixation points, they are unable to capture the torsional component of an ocular motility disease.

SUMMARY

In one implementation, a method is presented for determining ocular motor function in a patient. The patient is instructed to wear a pair of test glasses comprising a first lens having a first color and a second lens having a second color, where the first color and the second color differ. A light comprising a first color is projected onto a vertical surface, where the location of the light can be moved on the vertical surface. For each value of (i), an (i)th fixation point is then projected on the vertical surface, where the (i)th fixation point is one of (N) total fixation points and comprises the second color. For each value of (i), a perceived location is recorded upon receiving a signal that the (i)th fixation point is illuminated by the light. Finally, the (N) perceived locations are transformed into an ocular motor function map.

In another implementation, an article of manufacture is presented comprising a microprocessor and a computer readable medium comprising computer readable program code disposed therein for determining ocular motor function in a patient. The computer readable program code comprises a series of computer readable program steps to effect projecting a light comprising a first color onto a vertical surface, where a location of the light on a vertical surface can be moved, projecting, for each value of (i), an (i)th fixation point on the vertical surface, where the (i)th fixation point is one of (N) total fixation points, wherein the (i)th fixation point comprises a second color, where the first and second color differ, recording, for each value of (i), an (i)th perceived location upon receiving a signal that the (i)th fixation point is illuminated by the light, and transforming (N) perceived locations into an ocular motor function map.

In another implementation, a computer program product encoded in a computer readable medium is presented. The computer program product is useable with a programmable computer processor for determining ocular motor function in a patient and comprises computer readable program code which causes the programmable processor to project a light comprising a first color onto a vertical surface, where a location of the light on the vertical surface can be moved, to project, for each value of (i), an (i)th fixation point on the vertical surface, where the (i)th fixation point is one of (N) total fixation points, where the (i)th fixation point is a light comprising a second color, where the first and the second color differ, to record, for each value of (i), an (i)th perceived location upon receiving a signal that the (i)th fixation point is illuminated by the light, and to transform (N) perceived locations into an ocular motor function map.

In another implementation, a method of determining the torsional component of an ocular motility disease in a patient is presented. The method comprises instructing the patient to wear a pair of test glasses comprising a first lens having a first color and a second lens having a second color, where the first color and the second color differ. The method further comprises projecting a first asymmetric symbol comprising a first color onto a vertical surface and projecting, for each value of (i), an (i)th asymmetric symbol on the vertical surface, where the (i)th fixation point is one of (N) total fixation points, where the (i)th asymmetric symbol and the first asymmetric symbol are the same, where the (i)th asymmetric symbol is of a second color, wherein the first and second color differ;

In another implementation, an article of manufacture is presented, where the article of manufacture comprises a microprocessor and a computer readable medium comprising computer readable program code therein for determining a torsional component of an ocular motility disease in a patient. The computer readable program code comprises a series of computer readable program steps to effect projecting a first asymmetric symbol comprising a first color onto a vertical surface, projecting, for each value of (i), an (i)th asymmetric symbol on the vertical surface, where the (i)th fixation point is one of (N) total fixation points, where the (i)th asymmetric symbol and the first asymmetric symbol are the same, where the (i)th asymmetric symbol is of a second color, where the first and second color differ, recording an (i)th perceived location and an (i)th perceived orientation upon receiving a signal that the first asymmetric symbol is aligned with the (i)th asymmetric symbol, and transforming the (i)th perceived location and the (i)th perceived orientation into an ocular motor functioning map illustrating the torsional component of an ocular motility disease.

In another implementation, a computer program product encoded in a computer readable medium and useable with a programmable computer processor for determining a torsional component of an ocular motility disease in a patient is presented. The computer program product comprises computer readable program code which causes the programmable processor to project a first asymmetric symbol comprising a first color onto a vertical surface, to project, for each value of (i), an (i)th asymmetric symbol on the vertical surface, where the (i)th fixation point is one of (N) total fixation points, where the (i)th asymmetric symbol and the first asymmetric symbol are the same, where the (i)th asymmetric symbol is of a second color, where the first and second color differ, to record an (i)th perceived location and an (i)th perceived orientation upon receiving a signal that the first asymmetric symbol is aligned with the (i) th asymmetric symbol, and to transform the (i)th perceived location and the (i)th perceived orientation into an ocular motor functioning map illustrating the torsional component of an ocular motility disease.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
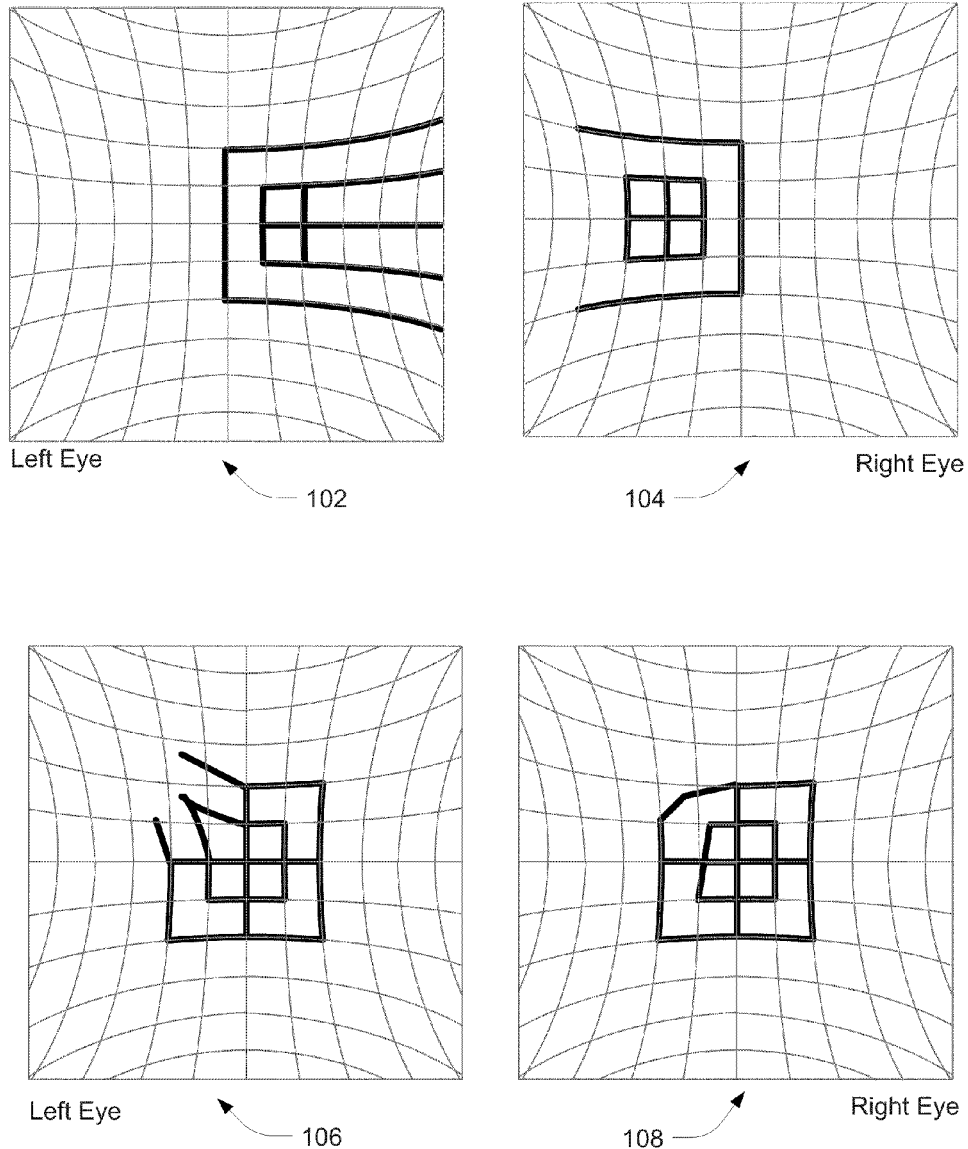
FIG. 1 shows typical chart records of a Hess Screen Test.
Figure 2A:
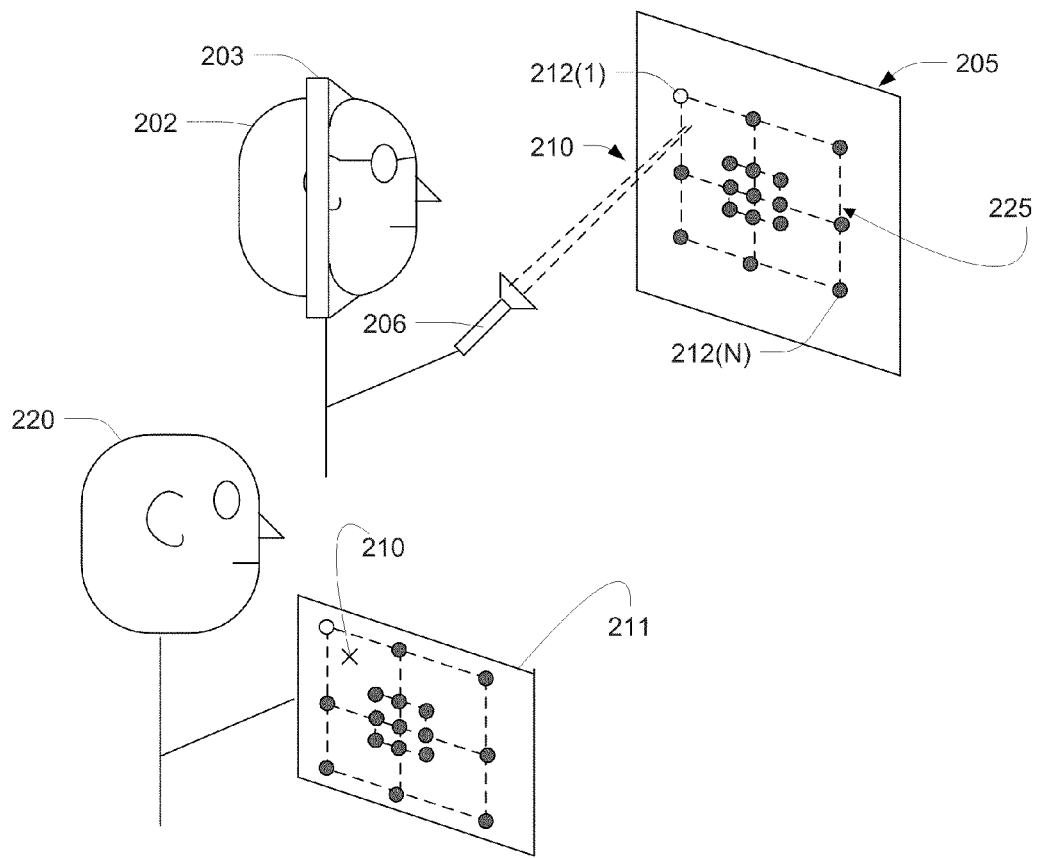
FIG. 2A is a block diagram illustrating a prior art method of performing a Hess Screen Test.
Figure 2B:
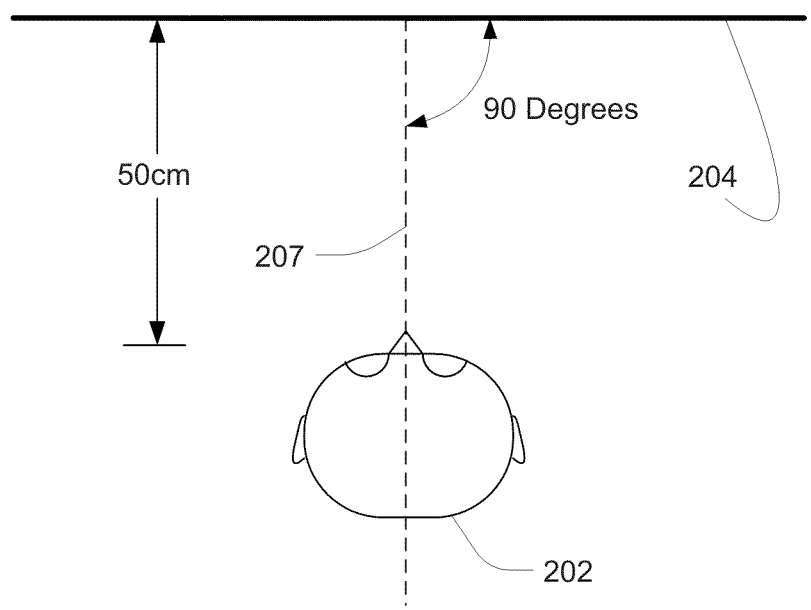
FIG. 2B is a block diagram illustrating a sagittal plane of the patient being perpendicular to the test screen.

Applicants' invention is illustrated in FIGS. 3-6B For illustrative purposes only, FIGS. 1, 2A, and 2B, are provided depicting the prior art methodology.

Referring now to FIGS. 2A and 2B, the prior art method of performing a Hess Screen Test is presented. A person skilled in the art will understand that the method of performing the Lancaster Red-Green Test is similar to the Hess Screen Test. In the illustrated embodiment of FIG. 2A, patient 202 is shown facing a Hess screen 205. Hess screen 205 is shown as comprising grid 225 which includes (N) fixation points 212, each fixation point being designated in red.

Superimposed on Hess screen 205 is a grid (not illustrated) consisting of horizontally and vertically curved lines produced by projecting the surface coordinates of a sphere onto a surface situated at the same distance of the radius of the sphere. When performing the test, examiner 220 positions patient 202 such that the patient 202's head is at the center of the sphere, frontoparallel to the projected area at a distance of approximately fifty centimeters (50 cm). As can be seen in FIG. 2B this requires that patient 202 is oriented such that nominal vertical plane 207 be perpendicular to screen 205, wherein nominal vertical plane 207 comprises a cranial portion of patient 202's sagittal plane.

Before performing the Hess Screen Test, examiner 220 must neutralize a head tilt or turn by patient 202 by placing patient 202 in the "forced (or controlled) primary position." A small head rotation to a side, and/or or a head tilt upwardly or downwardly may avoid or reduce the symptoms that would otherwise be caused by a paretic muscle by avoiding the field of action of the affected muscle. It may therefore be necessary to immobilize patient 202's head during the examination to achieve valid test results.

In the illustrated embodiment of FIG. 2A, the head of patient 202 is immobilized using head-stabilizing assembly 203. In certain embodiments, head-stabilizing assembly 203 includes a chin rest and a head rest. In certain embodiments, head-stabilizing assembly 203 includes side rests to prevent the head from moving towards either side. In certain embodiments, head-stabilizing assembly 203 includes a means for preventing patient 202's head from moving backwardly. In certain embodiments, one or more of the surfaces are adjustable such that a physician or technician can move or lock those surfaces into place to prevent movement of patient 202's head. In certain embodiments, a soft bite bar may be used in addition to or in place of head-stabilizing assembly 203. In certain embodiments, head-stabilizing assembly 203 is not used and examiner 220 instructs patient 202 not to move patient 202's head.

As illustrated in FIG. 2A, during the Hess test patient 202 wears a pair of glasses typically having one red lens and one green lens. Examiner 220 instructs patient 202 to use a light-emitting device 206 to shine green light 210 onto each of the red fixation points 212 in turn. The use of the colored lenses forces the dissociation of the eyes by filtering what can be seen by each eye. Patient 202 uses the red-lens eye to locate a designated fixation point 212(n), while the green-lens eye cannot see that fixation point. The patient then uses the green-lens eye to direct green light 210 onto the designated fixation point.

As will be clear to one of ordinary skill in the art, during the Hess test, light-emitting device 206 illuminates the circular fixation point with a dot of green light. As will also be clear to one of ordinary skill in the art, if the Lancaster Red-Green test was being performed instead, light emitting device 206 would include a cover or other means to illuminate a linear fixation point with a bar of green light.

After patient 202 has attempted to sequentially direct green light 210 onto each of the fixation points 212, examiner 220 instructs patient 202 to reverse the glasses and to perform the test again.

During the examination, examiner 220 records, by hand, the vertical and horizontal difference in the location of green light 210 and each fixation point 212(n). The record is made on a chart 211 which comprises a copy of grid 225. In the illustrated embodiment of FIG. 2A, the examiner 220 has placed an "X" onto chart 211 to indicate the location that patient 202 directed light 210 when attempting to direct light 210 onto fixation point 212(1). The recorded points are subsequently connected along the horizontally and vertically curved lines to form an inner and outer square. The skew of the resulting squares indicates under- or overaction by an extraocular muscle while the difference in shape of the inner and outer plots indicate the sources of incomitancy.

FIG. 1. presents several exemplary charts created by an examiner, such as examiner 220, during a Hess Screen Test. Charts 102 and 104 are exemplary ocular motor functioning charts for a patient having a paralysis of the sixth nerve. Charts 106 and 108 are exemplary ocular motor functioning charts for a patient having Brown's syndrome in the right eye.

Figure 3:
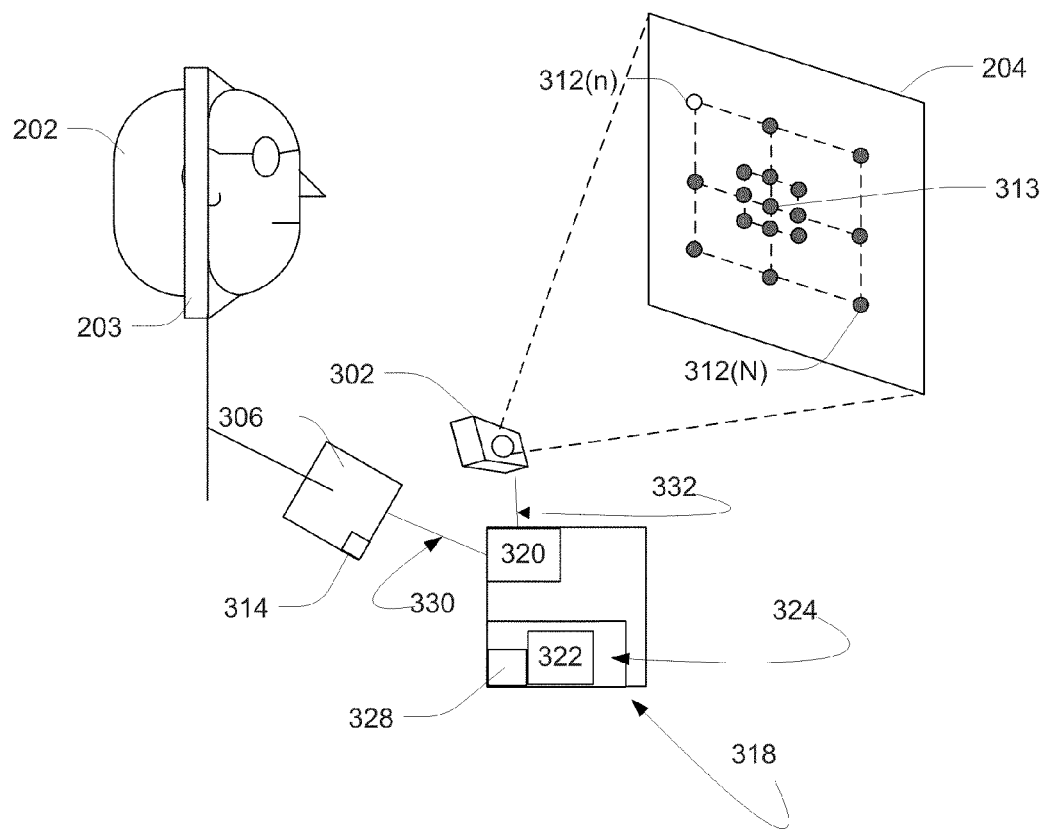
FIG. 3 is a block diagram illustrating an embodiment of a patient performing a Hess Screen Test according to the Applicants' invention.

FIG. 3 illustrates an embodiment of Applicant's apparatus and method to implement a Hess or Lancaster Red-Green test. Patient 202 is shown facing vertical surface 204 with patient 202's head fixed in head-stabilizing assembly 203.

In the illustrated embodiment of FIG. 3, a projector 302 is shown projecting (N) red fixation points 312 onto vertical surface 204. In certain embodiments, projector 302 is integral to computing device 318. In other embodiments, projector 302 is a peripheral device disposed on a table located adjacent patient 202. In other embodiments, projector 302 is a peripheral device disposed on the ceiling of an examination room.

In certain embodiments, fixation points 312 are circular. In certain embodiments, fixation points 312 are linear. In certain embodiments, fixation points 312 are asymmetric. In certain embodiments, a combination of linear, circular, and/or asymmetric fixation points are used.

In certain embodiments, vertical surface 204 is surrounded by a shield which blocks ambient light. In such embodiments, the shield may be a box. In such embodiments the shield may be a curtain. In such embodiments, the shield may be large enough to surround at least the patient's head, head stabilizing assembly 203, and projector 302. In such embodiments, the shield may be large enough to surround the patient's head and torso. In certain embodiments, the screen is located in a dark room such that when the test is being performed there is no ambient light.

In certain embodiments, projector 302 is calibrated based on the ambient lighting and/or color scales, intensities, and other variations to take into effect wall color, surface textures, planarity of the surface, and other surface variations of vertical surface 204. In such embodiments, projector 302 may be self-calibrating. In such an embodiment, projector 302 may calibrate based on the ambient light conditions before the start of each test. In such embodiments, the intensity of the projector 302 may be calibrated. In such embodiments, the color projected onto vertical surface 204 may be calibrated.

In certain embodiments, head-stabilizing assembly 203, projector 302, and computing device 318, are portable devices. In such embodiments, projector 302 may be battery powered. In such embodiments, projector 302 may be calibrated based on the strength of the battery. In certain embodiments, head-stabilizing assembly 203, where portable, weighs less than one-hundred (100) pounds.

Fixation points 312 are located along lines extending outwardly from center point 313 in (N) diagnostic positions of gaze at fifteen degrees (15°), and in (N) diagnostic positions of gaze at thirty degrees (30°). In certain embodiments, (N) equals two (2). In certain embodiments, (N) equals nine (9). In certain embodiments, Applicants' method utilizes less than a total number of fixation points 312 on vertical surface 204. By way of example and not limitation, two (2) fixation points 312 may be used for diagnosing a change in the ocular motor function of a patient. Alternatively, four (4) or more fixation points 312 may be used to diagnose a muscle palsy.

As described hereinabove, patient 202, with their head fixed within head-stabilizing assembly 203, wears a pair of glasses having one red lens and one green lens to force the dissociation of patient 202's eyes. In certain embodiments, patient 202 and head-stabilizing assembly 203 are positioned one (1) meter from vertical surface 204. In other embodiments, patient 202 and head-stabilizing assembly 203 are positioned less than one (1) meter from vertical surface 204. In other embodiments, patient 202 and head-stabilizing assembly 203 are positioned more than one (1) meter from vertical surface 204.

Patient 202 then attempts, using touchpad 306, illuminate seriatim each of the fixation points 312(n) with a green point projected by projector 302 as each fixation point 312(n) is projected onto vertical surface 204 by projector 302. As will be known by one of ordinary skill in the art, a touchpad, or trackpad, is a pointing device consisting of a specialized surface that can translate the motion and position of a user's fingers or stylus to a relative position of the projection on vertical surface 204. In yet other embodiments, patient 202 uses another type of tactile sensor.

In the illustrated embodiment of FIG. 3, touchpad 306 includes trigger 314 and wireless communication interface 308. In certain embodiments, patient 202 engages trigger 314 when the patient perceives that a green symbol projected by projector 302 is centered on an illuminated fixation point 312(n). In certain embodiments, touchpad 306, synchronously with activation of trigger 314, provides a signal to computing device 318 via communication link 330. In certain embodiments, computing device 318 is in communication with projector 302 via communication link 332.

In certain embodiments, touchpad 306, synchronously with activation of trigger 314, provides a wireless signal using wireless communication interface 308 to wireless communication interface 316 of computing device 318.

In certain embodiments, trigger 314 is a button. In certain embodiments, trigger 314 is a finger trigger. In yet other embodiments, trigger 314 is a switch.

When activated, trigger 314 causes touchpad 306 to send an activation signal via wireless communication interface 308 to computing device 318. Synchronously upon receipt of an activation signal, computing device 318 records the location and/or orientation of the projected green symbol.

In certain embodiments, computing device 318 is selected from the group consisting of an application server, a web server, a work station, a personal computer, iPad, or other like device from which information can be stored and/or processed. In certain embodiments, computing device 318 is interconnected to other computing devices using a data communication fabric via Small Computer Systems Interface ("SCSI") protocol running over a Fibre Channel ("FC") physical layer. In certain embodiments, the data communication fabric comprises one or more data switches. In certain embodiments, the data communication fabric is a wide area network ("WAN"). In certain embodiments, the data communication fabric is a local area network ("LAN"). In other embodiments, the connections between computing device 318 and other computing devices comprise other protocols, such as Infiniband, Ethernet, or Internet SCSI ("iSCSI").

In the illustrated embodiment of FIG. 3, computing device 318 comprises an operating system 322, non-transitory computer readable medium 324, and processor 320. In certain embodiments computer readable medium 324 includes instructions 328. In certain embodiments, operating system 322 is encoded in computer readable medium 324.

As those skilled in the art will appreciate, computing device 318 comprises additional elements and features not shown in FIG. 3.

In certain embodiments, computer readable medium 324 comprises a magnetic information storage medium, an optical information storage medium, an electronic information storage medium, and the like. By "magnetic storage medium," it is meant, for example, a device such as a hard disk drive, floppy disk drive, or magnetic tape. By "optical information storage medium," it is meant, for example, a Digital Versatile Disk ("DVD"), High-Definition DVD ("HD-DVD"), Blu-Ray Disk ("BD"), Magneto-Optical ("MO") disk, Phase-Change ("PC") disk, etc. By "electronic storage media" it is meant, for example, a device such as PROM, EPROM, EEPROM, Flash PROM, compactflash, smartmedia, and the like. In certain embodiments, memory 324 comprises a magnetic information storage medium, and optical information storage medium, an electronic information storage medium, and the like.

In addition to fixing a patient 202's head such that the their cranial sagittal plane is perpendicular to vertical surface 204, in certain embodiments, head-stabilizing assembly 203 can be used to further correct for the testing environment. In such embodiment, head-stabilizing assembly 203 may further comprise an inclinometer. As those skilled in the art will appreciate, an inclinometer is an instrument for measuring angles of slope (or tilt), or inclination of an object with respect to gravity. In these embodiments, the inclinometer element of head-stabilizing assembly 203 determines whether head-stabilizing assembly 203 is tilted in either direction. In such embodiments, head-stabilizing assembly 203 provides an alert to notify a doctor, nurse, or other test administrator to adjust head-stabilizing assembly 203 when head-stabilizing assembly 203 is tilted.

In certain embodiments, head-stabilizing assembly 203 further includes two or more laser range finders. As those skilled in the art will appreciate, a laser range finder is a device which uses a laser beam to determine the distance to an object. Wherein two or more laser range finders are used, whether head-stabilizing assembly 203 is oriented such that a cross-sectional plane of head-stabilizing assembly 203 is perpendicular to vertical surface 204 can be determined. In such embodiments, head-stabilizing assembly 203 provides an alert to notify a doctor, nurse, or other test administrator to adjust head-stabilizing assembly 203 when head-stabilizing assembly 203 is not parallel to vertical surface 204.

In certain embodiments, head-stabilizing assembly 203 further performs a verification test to determine if there is a horizontal, vertical, and/or rotational deviation for any of the (N) fixation points when they are illuminated by a projected point from projector 302. In such embodiments, head-stabilizing assembly 203 illuminates each of the (N) projected points and records the position of the illuminated point relative to the projected point. In certain such embodiments, head-stabilizing assembly 203 provides an alert to notify a doctor, nurse, or other test administrator to adjust head-stabilizing assembly 203 when the deviation between the illuminated point and the projected point is outside a threshold.

In certain embodiments, computing device 318 utilizes data provided by head-stabilizing assembly 203 to calculate a correction factor. In certain embodiments, computing device 318 determines a correction factor for each of the (N) projected points 312. In certain embodiments, computing device 318 applies the correction factor for head rotation and/or head tilt due to improper orientation of head-stabilizing assembly 203 or due to irregularities in the projection and/or illumination of each of the (N) fixation points 312.

In certain embodiments, computing device 318 uses all (N) recorded locations to create an ocular motor functioning chart for each eye, such as ocular motor functioning charts 102, 104, 106, and 108 (FIG. 1). In certain embodiments, computing device 318, uses all (N) corrected locations to create a corrected ocular motor functioning chart for each eye.

Figure 4A:
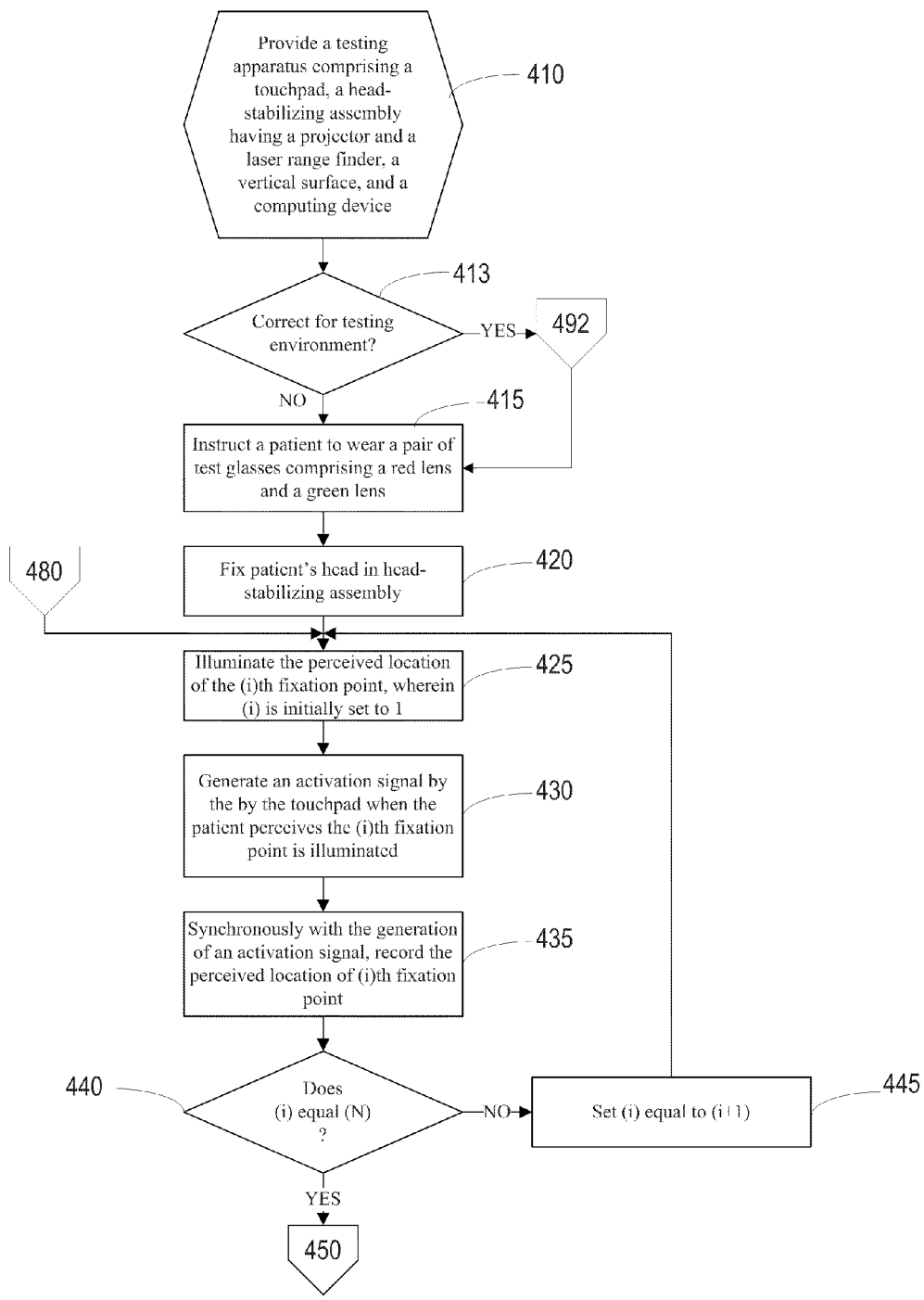
FIG. 4A is a flow chart summarizing the initial steps of an embodiment of Applicants' invention.
Figure 4B:
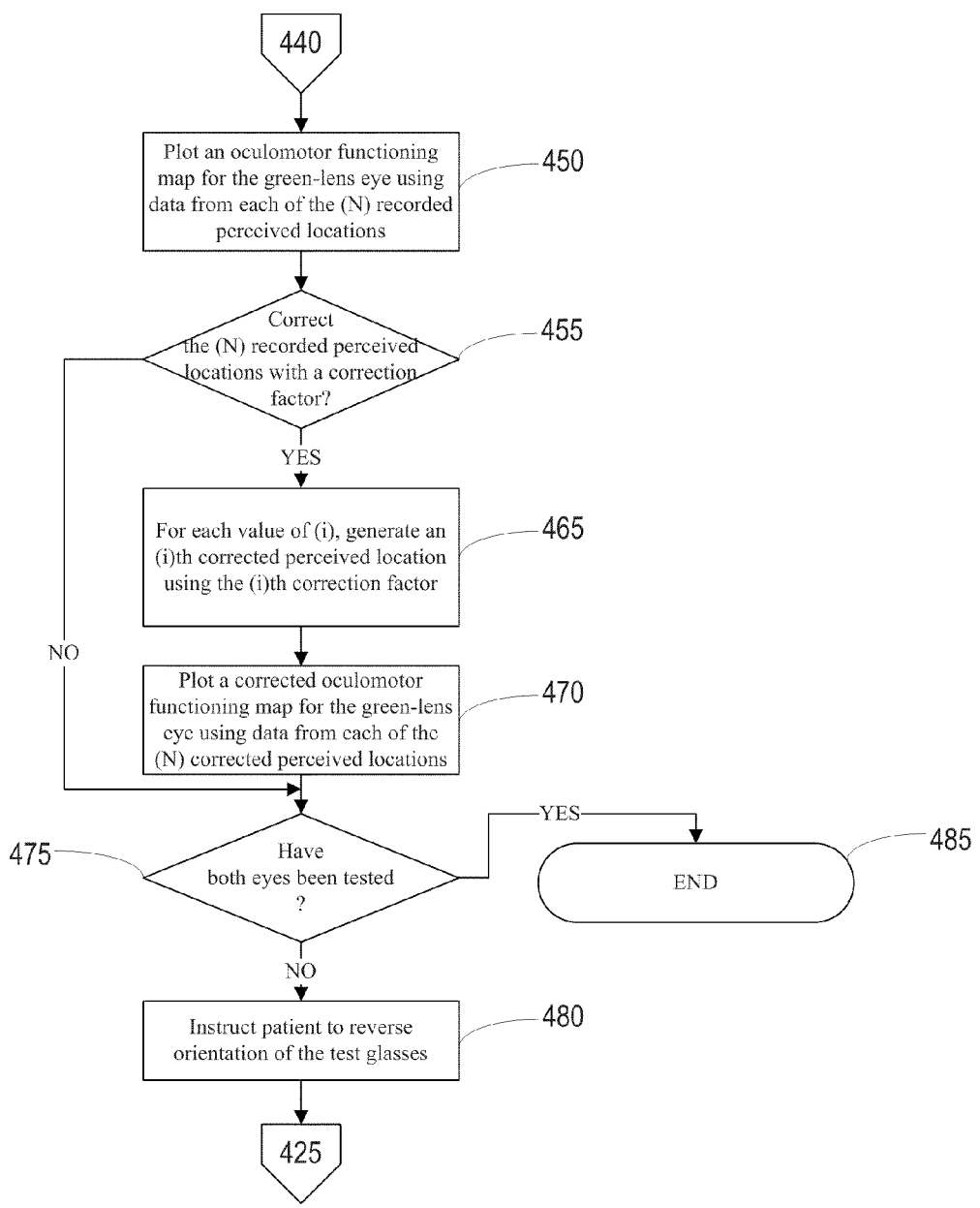
FIG. 4B is a flow chart summarizing additional steps of an embodiment of Applicants' invention.
Figure 4C:
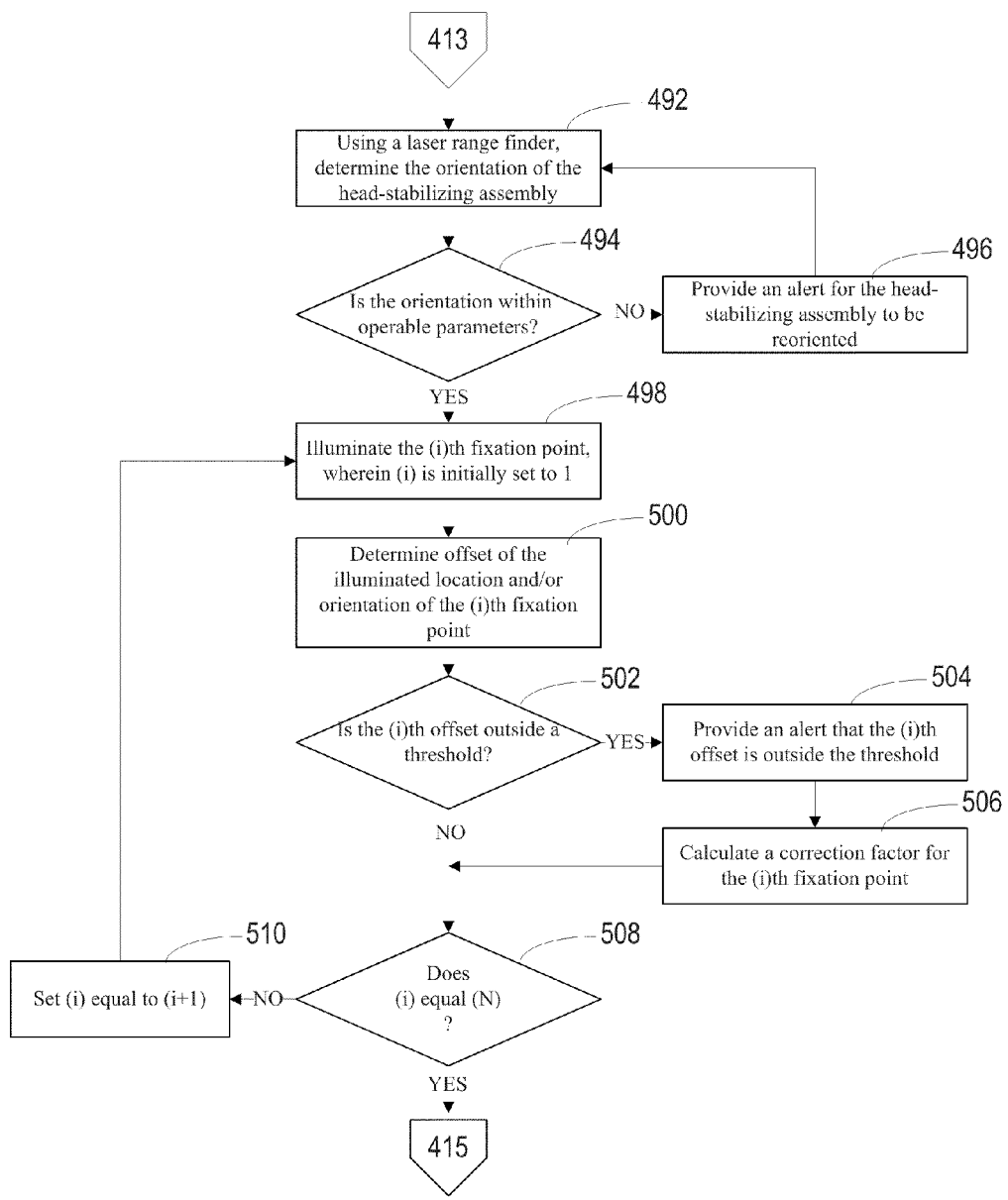
FIG. 4C is a flow chart summarizing additional steps of an embodiment of Applicants' invention.

FIGS. 4A, 4B, and 4C summarize Applicants' method which utilizes Applicants' apparatus. Referring now to FIG. 4A, in block 410 the method provides a testing apparatus comprising a touchpad, a head-stabilizing assembly having a projector, a vertical surface, and a computing device. In certain embodiments, the touchpad, head-stabilizing unit, and vertical surface can be used for performing a Hess test. In certain embodiments, the touchpad, head-stabilizing unit, and vertical surface can be used for performing a Lancaster Red-Green test. In certain embodiments, the touchpad, head-stabilizing unit, and vertical surface can be used with either the Hess or the Lancaster Red-Green test.

In certain embodiments the head-stabilizing assembly of block 410 further comprises a laser range finder. In such embodiments, in block 413, a check is made regarding whether Applicants' apparatus should correct for the testing environment. If yes, the method proceeds to block 490. Turning now to FIG. 4C, the computing device of block 410, using the laser range finder, determines the orientation of the head-stabilizing assembly relative to the vertical surface upon which the test will be projected, as indicated by block 494. If the orientation is not within operable parameters, an alert is provided to the test administer notifying them that the head-stabilizing assembly should be reoriented before proceeding with the test, as indicated by blocks 494 and 496. In certain embodiments, the alert is an audible alert. In certain embodiments, the alert is a visual alert. In such embodiments, the alert may be projected on to the vertical surface by the projector of the head-stabilizing assembly. In other embodiments, the alert may be displayed on a screen, such as a computer screen, connected to or otherwise in communication with the computing device. The method then proceeds at block 492 after the head-stabilizing assembly has been reoriented.

If the orientation is within operable parameters, then the method proceeds at block 498, whereby the computing device of block 410 instructs the projector of the head-stabilizing assembly of block 410 to sequentially illuminate each of the projected fixation points to correct for any error due to the testing environment or equipment malfunction. As is indicated by block 498, the projection of the (i)th fixation point is illuminated, where (i) is initially set to 1. An offset is then determined by the computing device between the projection of the (i)th fixation point and the place illuminated, as indicated by block 500. if the (i)th offset is outside a threshold an alert is provided to the test administrator, as indicated by blocks 504 and 502. As with the previous alert, the alert may be audible or visual. A correction factor may then be calculated for the (i)th fixation point, as indicated by block 506.

In block 508, a check is performed to determine if each of the (N) fixation points have been tested and a correction factor determined, if needed. If no, then (i) is set equal to (I+1) and the method returns to block 498. If all the fixation points have been tested, then the method returns to block 415 and continues as described herein.

Returning to FIG. 4A, in block 415 a patient is instructed to wear a pair of test glasses comprising a first lens having a first color and a second lens having a second color. In certain embodiments, the first or second color is red and the other color is green. In other embodiments, the first or second color is red and the other color is blue. In yet other embodiments, the first or second colors are any complementary colors.

In block 420, the patients head is secured within Applicants' head-stabilizing assembly. In certain embodiments, the head-stabilizing assembly of block 420 comprises a wireless communication interface. In certain embodiments, the head-stabilizing of block 420 comprises an inclinometer.

The patient's head is oriented within Applicants' head-stabilizing assembly such that the patient's cranial sagittal plane is perpendicular to the test screen of block 410, and such that the patient's cranial transverse plane is perpendicular to the test screen of block 410. In certain embodiments wherein the head-stabilizing assembly comprises an inclinometer, in block 420 the method generates a reference inclinometer value and provides that reference inclinometer value to the computing device of block 410, and the computing device encodes that reference inclinometer value in a computer readable medium.

In block 425, an (i)th fixation point is projected onto the vertical surface of block 410 by the projector of the head-stabilizing assembly, wherein (i) is initially set to 1, and wherein (i) is greater than or equal to 1 and less than or equal to (N).

In certain embodiments, the fixation points are circular. In certain embodiments, the fixation points are rectangular. In certain embodiments, the fixation points can be either circular or rectangular. In certain embodiments, some of the fixation points are rectangular while some are circular. In certain embodiments, one or more of the fixation points are asymmetric.

In block 430, the patient, using the touchpad, attempts to center a green-colored light generated by the projector of the head-stabilizing assembly of block 410 onto the fixation point of block 425. In certain embodiments, the projector projects a green-colored, circularly-shaped light onto the vertical surface of block 410. In certain embodiments, the projector projects a green-colored, rectangular-shaped light onto the vertical surface of block 410. in yet other embodiments, the projector projects a green-colored, asymmetrically shaped light onto the vertical surface of block 410.

In embodiments wherein the fixation point is circular, the projector of the head-stabilizing assembly projects a circularly-shaped green light. In these embodiments, the patient attempts to center the circular green light onto the circular fixation point using the touchpad of block 410. Similarly, In embodiments wherein the fixation point is rectangular or asymmetric, the projector of the head-stabilizing assembly projects a rectangular-shaped or asymmetric green light, respectively. In these embodiments, the patient attempts to center the rectangular-shaped or asymmetric-shaped green light onto the rectangular fixation point using the touchpad.

Further in block 430, the touchpad of block 410 is caused to generate an activation signal when the patient perceives a green light emitted by the projector of the head-stabilizing assembly of block 410 is centered upon the projected fixation point of block 425. In certain embodiments, the activation signal of block 430 is generated when the patient activates a trigger portion of the touchpad. In these embodiments, when the patient perceives a green light centered upon the projected fixation point of block 425, the patient depresses a trigger on the touchpad, thereby causing the touchpad to generate the activation signal of block 430. In other embodiments, the activation signal of block 430 is generated when the patient taps the touchpad. In these embodiments, when the patient perceives a green light centered upon the projected fixation point of block 425, the patient taps the surface of the touchpad, thereby causing the touchpad to generate the activation signal In block 435, synchronously with the generation in block 430 of an activation signal, the computing device of block 410 records the perceived location of the (i)th fixation point. In other embodiments, the perceived location of the (i)th fixation point is recorded by the projector of the head-stabilizing assembly of block 410.

In block 440, the method determines if all (N) fixation points have been illuminated, i.e. if (i) equals (N). In certain embodiments, block 440 is performed by the computing device of block 410.

If the method determines in block 440 that fewer than all (N) fixation points have been illuminated, then the method transitions from block 440 to block 445 wherein (i) is set equal to (I+1). In certain embodiments, block 445 is performed by the computing device of block 410. The method transitions from block 445 to block 425 and continues as described herein.

If the method determines in block 440 that all (N) fixation points have been illuminated, then the method transitions from block 440 to block 450 of FIG. 4B wherein the method plots an ocular motor functioning map for the green-lens eye using data from each of the (N) recorded perceived locations. In certain embodiments, block 450 is performed by the computing device of block 410.

In block 455, the method determines whether to correct the (N) recorded perceived locations of block 435 for environmental conditions or equipment malfunction. In certain embodiments, block 455 is performed by the computing device of block 410. In certain embodiments, block 455 is performed by a system operator.

If the method elects in block 455 not to correct the (N) recorded perceived locations of block 435 for environmental conditions and/or equipment malfunction, then the method transitions from block 455 to block 475. Alternatively, if the method elects in block 455 to correct the (N) recorded perceived locations of block 435 for environmental conditions and/or equipment malfunction, then the method transitions from block 455 to block 465 wherein, for each value of (i), an (i)th corrected perceived location is generated using the (i)th correction factor of block 506. In certain embodiments, block 465 is performed by the computing device of block 410.

In block 470, the method plots a corrected ocular motor functioning map for the green-lens eye using data from each of the (N) corrected perceived locations of block 465.

In block 475, the method determines if both the patient's eyes have been tested. In certain embodiments, block 475 is performed by the computing device of block 410.

If the method determines in block 475 that both the patient's eyes have been tested, then the method transitions from block 475 to block 485 and ends. Alternatively, if the method determines in block 475 that both the patient's eyes have not been tested, then the method transitions from block 475 to block 480 wherein the patient is instructed to reverse the orientation of the test glasses of block 410, i.e. if the patient's left eye was previously the green-lens eye, then the patient repositions the test glasses such that the patient's right eye becomes the green-lens eye. The method transitions from block 480 to block 425 and continues as described herein.

In certain embodiments, Applicants' method described above in connection with FIGS. 4A, 4B, and 4C is used to perform the Hess test. In certain embodiments, Applicants' method is used to perform the Lancaster Red-Green test. In certain embodiments, Applicants' method performs both the Hess test and the Lancaster Red-Green test in succession. In certain embodiments, Applicants' method begins by performing the Hess test and switches to the Lancaster Red-Green test upon indication that the patient has a torsional deficiency. In certain embodiments, Applicants' method begins by performing the Hess test and switches to the Lancaster Red-Green test upon some other indication. In certain embodiments, Applicants method begins by performing the Lancaster Red-Green test and switches to the Hess test.

In certain embodiments, individual processes described in connection with FIGS. 4A, 4B, and 4C may be combined, eliminated, or reordered.

In certain embodiments, instructions, such as instructions 328 (FIG. 3), are encoded in computer readable medium, such as memory 324 (FIG. 3), wherein those instructions are executed by a processor, such as processor 320 (FIG. 3), to perform one or more of the blocks 413, 425, 430, 435, 440, 445, 450, 455, 465, 470, 475, 492, 494, 496, 498, 500, 502, 504, 506, 508, and/or 510 recited in FIGS. 4A, 4B and 4C.

In yet other embodiments, the invention includes instructions residing in any other computer program product, where those instructions are executed by a computer external to, or internal to, computing device 318 (FIG. 3) to perform one or more of the blocks 413, 425, 430, 435, 440, 445, 450, 455, 465, 470, 475, 492, 494, 496, 498, 500, 502, 504, 506, 508, and/or 510 recited in FIGS. 4A, 4B and 4C. In either case the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

As will be understood by one of ordinary skill in the art, a Hess or Lancaster Red-Green Test, as taught by the prior art, is unable to capture the torsional component of ocular motility disorders. By ocular motility disorders, Applicants means those disorders where impairment of eye movements is a primary manifestation of the disease. Where a torsional component is present, a patient's vision will be rotated either clockwise or counterclockwise.

Figure 5A:
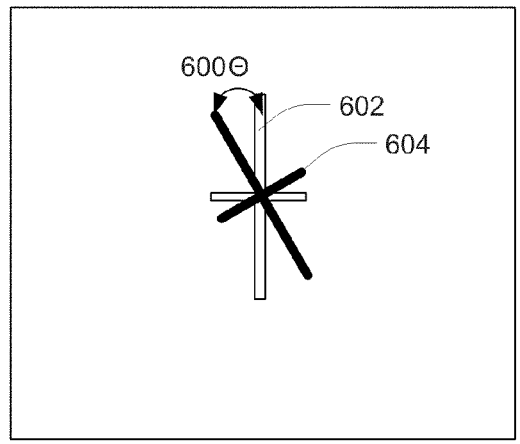
FIG. 5A is a block diagram illustrating the torsional component of an ocular motility disease.
Figure 5B:
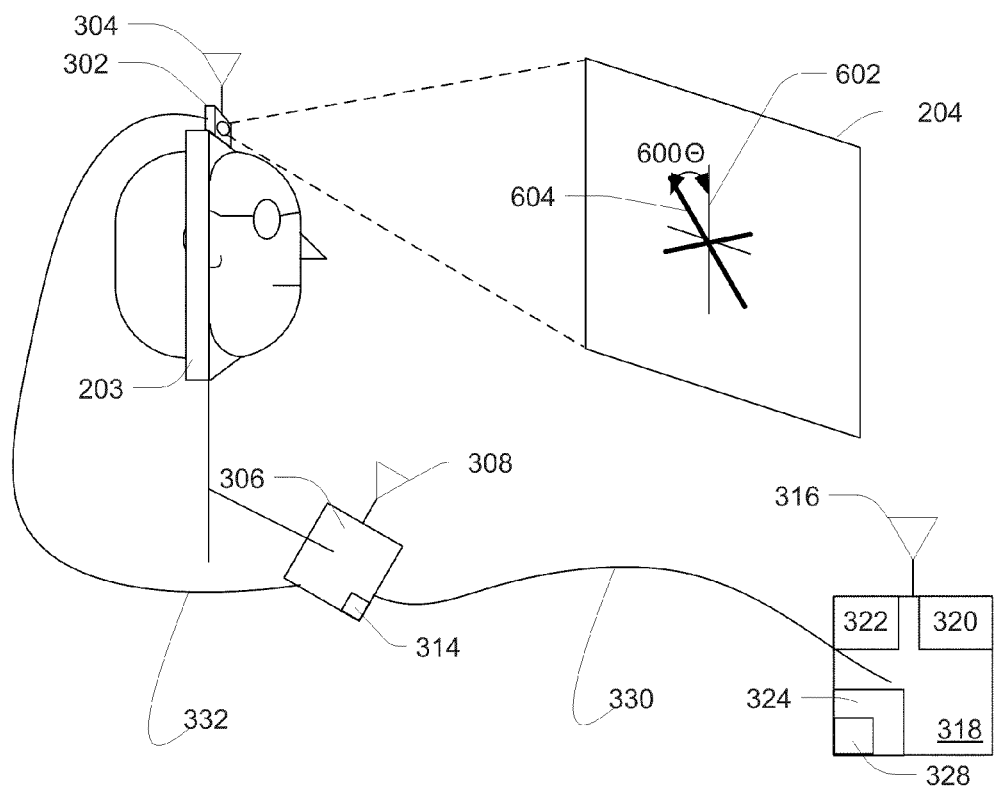
FIG. 5B is a block diagram illustrating an embodiment of a patient performing a test for the torsional component of an ocular motility disease.

Referring now to FIGS. 5A and 5B, in certain embodiments Applicant's invention is able to further measure the torsional component of ocular motility disorders and characterize the direction of that torsional component, wherein the torsional component causes a patient's vision to be rotated by an angle θ. In such embodiments, an asymmetric symbol 602 is projected on vertical surface 204. Patient 202 is then instructed to align a second projected asymmetric symbol 604 over symbol 602 using touchpad 306. Computing device 318 then determines the rotational angle 600, wherein rotational angle 600 is a measurement of the torsional component of an ocular motility disorder.

In certain embodiments, patient 202 uses touchpad 306 to align symbol 604 over symbol 602. In such embodiments, patient 202 may press trigger 314 or tap on the touchpad to cause projector 302, in communication with touchpad 306, to project symbol 604.

In such embodiments, when patient 202 activates trigger 314 or taps on touchpad 306, touchpad 306 sends an activation signal via wireless communication interface 308 and/or communication link 330 to projector 302. Synchronously upon receipt of the activation signal, computing device 318 records and stores the location and orientation of symbol 604 relative to symbol 602.

In other embodiments, patient 202 uses an input device other than a touchpad to align symbol 604 over symbol 602. In such embodiments, the input device may be a keyboard, projected keyboard, keypad, keyer, mouse, joystick, pointing stick, remote, paddle, or any other known input means for a computer. In such embodiments, patient 202 may use one button of the input device to rotate symbol 604 counterclockwise and another button to rotate symbol 604 clockwise.

Projector 302 and/or touchpad 306 provides the recorded position and orientation of symbol 604 via wireless communication interface 304 or via wireless communication interface 308 to wireless communication interface 316 of computing device 318. Computing device 318 then determines the rotational angle 600 from patient 202's use of touchpad 306 to align symbol 604 with symbol 602.

In embodiments where computing device 318 has further determined a correction factor for the fixation points to account for any environmental factors or mechanical malfunctions, computing device 318 further adjusts rotational angle 600 to account for the correction factor.

Figure 6A:
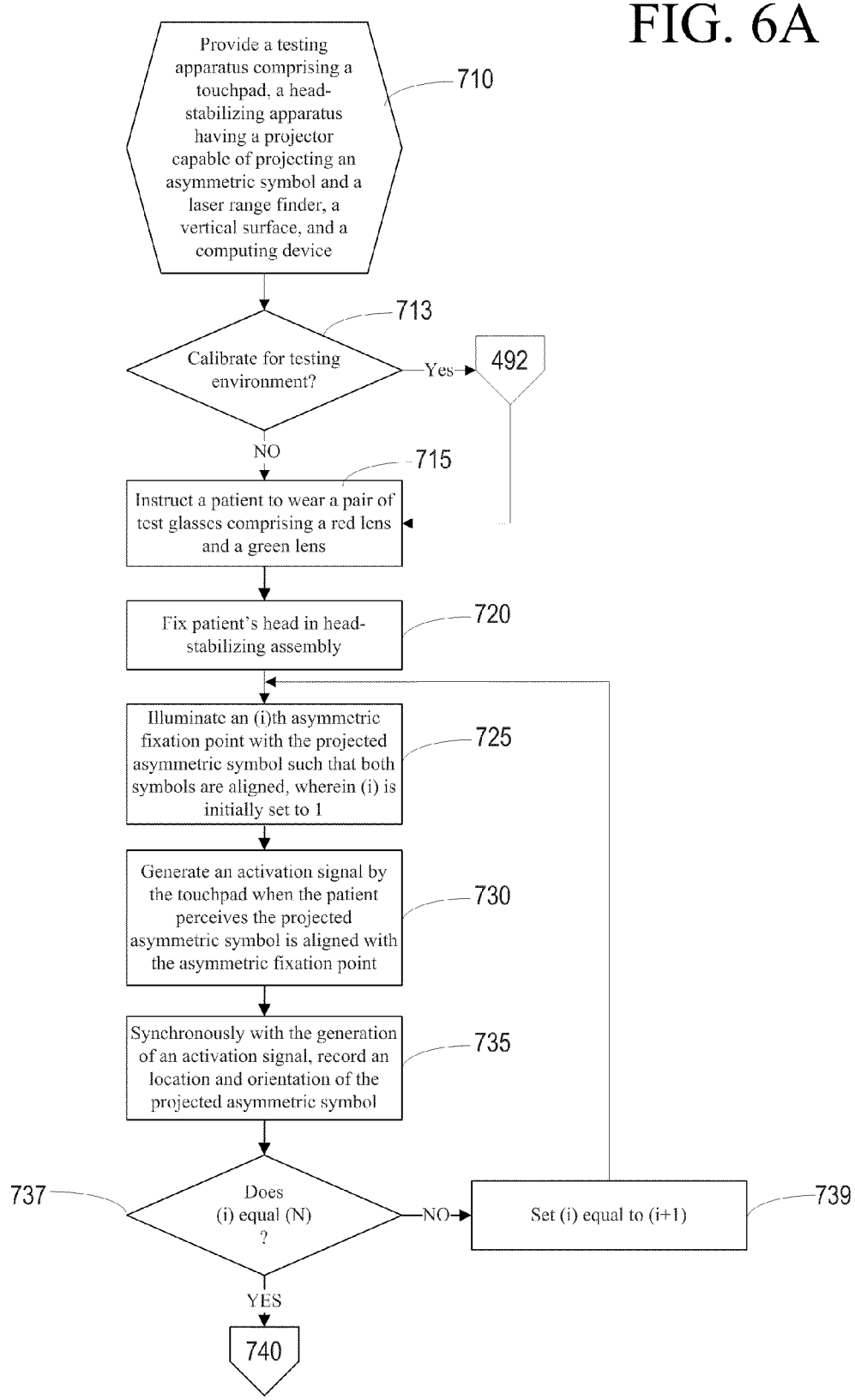
FIG. 6A is a flow chart summarizing the initial steps of an embodiment of Applicants' invention.
Figure 6B:
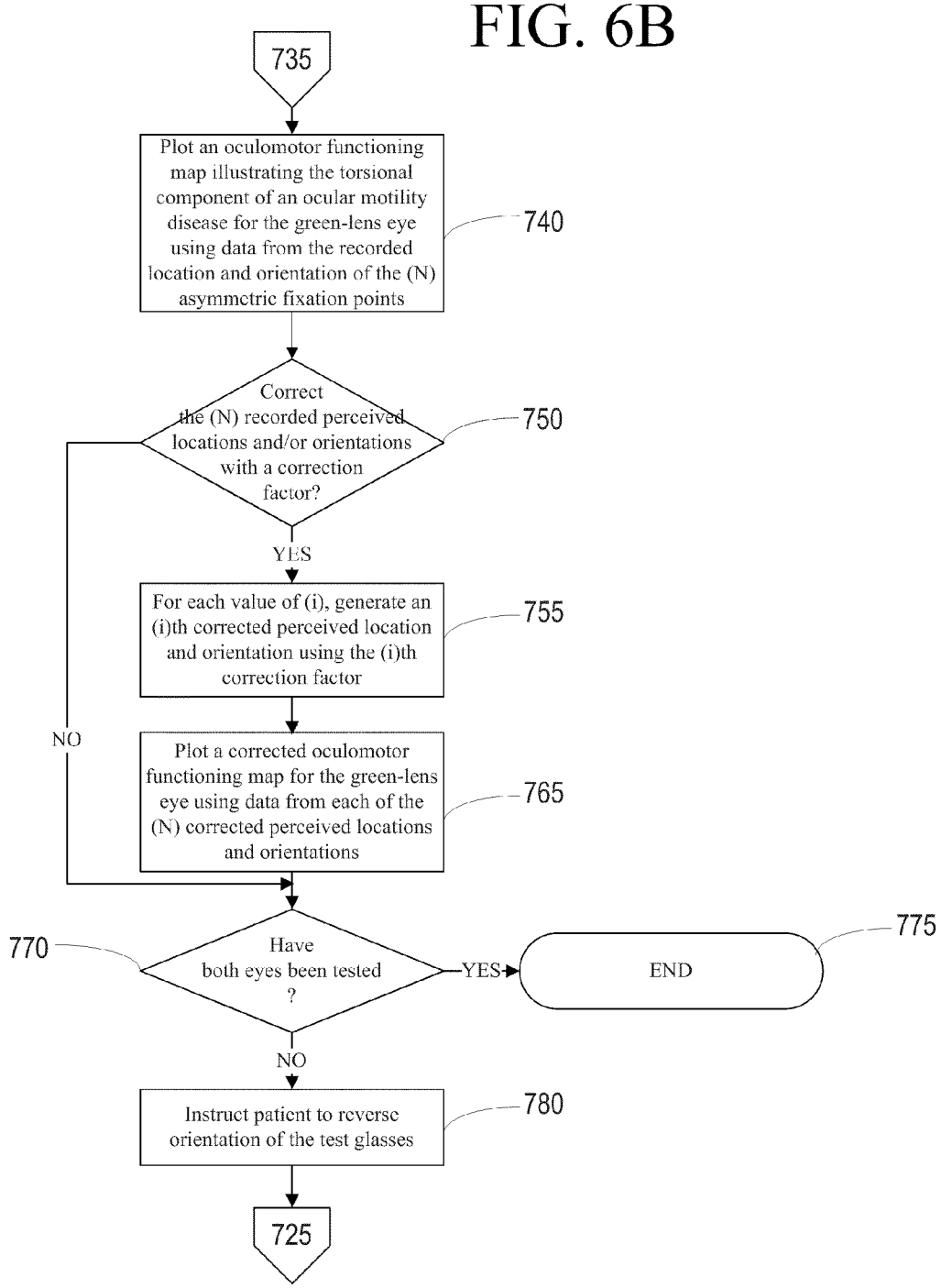
FIG. 6B is a flow chart summarizing additional steps of an embodiment of Applicants' invention.

FIGS. 6A and 6B summarize an embodiment of Applicants' method which utilizes Applicants' apparatus to determine the torsional component of an ocular motility disease. Referring now to FIG. 6A, in block 710 the method provides a testing apparatus comprising a touchpad, a head-stabilizing apparatus having a projector capable of projecting an asymmetric symbol, a vertical surface, and a computing device.

In certain embodiments the head-stabilizing assembly of block 710 further comprises a laser range finder. In such embodiments, in block 712, a check is made regarding whether Applicants' apparatus should correct for the testing environment. If yes, the method proceeds to block 490 of FIG. 4C as previously described herein. If no correction is performed or once the correction is completed, the method returns to block 715.

In block 715, a patient is instructed to wear a pair of test glasses comprising a first lens having a first color and a second lens having a second color. In certain embodiments, the first or second color is red and the other color is green. In other embodiments, the first or second color is red and the other color is blue. In yet other embodiments, the first or second colors are any complementary colors.

In block 720, a patient's head is fixed within Applicants' head-stabilizing apparatus. In certain embodiments, the head-stabilizing apparatus of block 710 comprises a wireless communication interface. In certain embodiments, the c head-stabilizing apparatus of block 710 comprises an inclinometer.

In block 725, the projector of the head-stabilizing assembly of block 710 projects the (i)th asymmetric fixation point. The patient then attempts to align a green-colored asymmetric symbol also projected by the projector of the head-stabilizing assembly onto the (i)th asymmetric fixation point.

In block 730, the touchpad of block 710 is caused to generate an activation signal when the patient perceives the green asymmetric symbol emitted by the device is aligned with the illuminated (i)th asymmetric fixation point of block 725. In certain embodiments, the activation signal of block 730 is generated when the patient activates a trigger portion of the touchpad. In these embodiments, when the patient perceives the green asymmetric symbol is aligned with the (i)th asymmetric fixation point I of block 725, the patient depresses a trigger on the touchpad, thereby causing the touchpad to generate the activation signal of block 730. In other embodiments, the activation signal of block 730 is generated when the patient taps the touchpad. In these embodiments, when the patient perceives the green asymmetric symbol is aligned with the (i)th asymmetric fixation point of block 725, the patient taps the touchpad, thereby causing the touchpad to generate the activation signal of block 730.

In block 735, the method synchronously with the generation in block 730 of an activation signal, records the (i)th location and orientation of the green asymmetric symbol using the computing device of block 710. In certain embodiments, the activation signal of block 730 comprises a wireless activation signal.

In block 737, a check is made to determine if all (N) of the asymmetric fixation points have been tested. If not, in block 739 (i) is set equal to (i+1) and the method proceeds from block 725 as described herein. If all (N) asymmetric fixation points have been tested, the method proceeds to block 740 of FIG. 6B.

Turning to FIG. 6B in block 740 the method plots an ocular motor functioning map illustrating the torsional component of an oculor motility disease for the green-lens eye using data from the (N) recorded locations and orientations of block 735. In certain embodiments, block 740 is performed by the computing device of block 710.

In block 750, the method determines whether to correct each of the (N) recorded locations and/or orientations of block 735 for environmental factors or mechanical malfunction. In certain embodiments, block 750 is performed by the computing device of block 710. In certain embodiments, block 750 is performed by a system operator.

If the method elects in block 750 not to correct the recorded image of block 735 with a correction factor, then the method transitions from block 750 to block 770. Alternatively, if the method elects in block 750 to correct each of the (N) recorded locations and/or orientations of block 735 for head rotation and/or head tilt, then the method transitions from block 750 to block 755 wherein, for each of the (N) recorded locations and/or orientations, the method generates an (i)th corrected locations and orientation using the (i)th correction factor. In certain embodiments, block 755 is performed by the computing device of block 710.

In block 765, the method plots a corrected ocular motor functioning map illustrating the torsional component of an ocular motility disease for the green-lens eye using data from the (N) corrected locations and orientations of block 760. In certain embodiments, block 755 is performed by the computing device of block 710.

In block 770, the method determines if both the patient's eyes have been tested. In certain embodiments, block 770 is performed by the computing device of block 710.

If the method determines in block 770 that both the patient's eyes have been tested, then the method transitions from block 770 to block 775 and ends. Alternatively, if the method determines in block 770 that both the patient's eyes have not been tested, then the method transitions from block 770 to block 780 wherein the patient is instructed to reverse the orientation of the test glasses of block 710, i.e. if the patient's left eye was previously the green-lens eye, then the patient repositions the test glasses such that the patient's right eye becomes the green-lens eye. The method transitions from block 780 to block 725 and continues as described herein.

One of ordinary skill in the art will further appreciate that, although described separately, the method described in relation to FIGS. 7A and 7B may be combined with the method described in relation to FIGS. 4A and 4B, such that the torsional component is tested at the same time as the spacial component is tested or immediately preceding or proceeding such testing. In such embodiments, both the torsional component and the spacial component may be plotted on the same oculor motor functioning map.

In certain embodiments, individual processes described in connection with FIGS. 7A and 7B may be combined, eliminated, or reordered.

In certain embodiments, instructions, such as instructions 328 (FIG. 3), are encoded in computer readable medium, such as memory 324 (FIG. 3), wherein those instructions are executed by a processor, such as processor 320 (FIG. 3), to perform one or more of the blocks 713, 725, 730, 735, 737, 739, 740, 745, 750, 755, 765, 770, 775 and/or 780 recited in FIGS. 7A and 7B.

In yet other embodiments, the invention includes instructions residing in any other computer program product, where those instructions are executed by a computer external to, or internal to, computing device 318 (FIG. 3) to perform one or more of the blocks 713, 725, 730, 735, 737, 739, 740, 745, 750, 755, 765, 770, 775 and/or 780 recited in FIGS. 7A and 7B. In either case the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

While the preferred embodiments of the present invention have been illustrated in detail, it should be apparent that modifications and adaptations to those embodiments may occur to one skilled in the art without departing from the scope of the present invention.

What is claimed is:

1. An article of manufacture comprising a microprocessor and a computer readable medium comprising computer readable program code disposed therein for determining a torsional component of an ocular motility disease in a patient, the computer readable program code comprising a series of computer readable program steps to effect:
   projecting a first asymmetric symbol comprising a first color onto a vertical surface;
   projecting, for each value of (i), an (i)th asymmetric symbol on the vertical surface, wherein the (i)th fixation point is one of (N) total fixation points, wherein the (i)th asymmetric symbol and the first asymmetric symbol are the same, wherein the (i)th asymmetric symbol is of a second color, wherein the first and second color differ, wherein (N) is greater than 1, and wherein (i) is greater than or equal to 1 and less than or equal to (N);
   recording an (i)th perceived location and an (i)th perceived orientation upon receiving a signal that the first asymmetric symbol is aligned with the (i)th asymmetric symbol; and
   transforming the (i)th perceived location and the (i)th perceived orientation into an ocular motor functioning map illustrating the torsional component of an ocular motility disease.

2. The article of manufacture of claim 1, wherein:
   said first asymmetric symbol comprises two crossing lines that define four arms; three of said four arm comprise a first length;
   a fourth arm comprises a second length; and
   said first length differs from said second length.

3. The article of manufacture of claim 1, further comprising a series of computer readable steps to effect, for each value of (i), determining an (i)th rotational angle of the first asymmetric symbol to the (i)th asymmetric symbol.

4. The article of manufacture of claim 1, further comprising a series of computer readable steps to effect, for each value of (i), determining an (i)th correction factor.

5. The article of manufacture of claim 4, further comprising a series of computer readable steps to effect, for each value of (i), transforming the (i)th perceived location into an (i)th corrected perceived location and the (i)th perceived orientation into an (i)th corrected perceived orientation using the (i)th correction factor.

6. The article of manufacture of claim 5, further comprising a series of computer readable steps to effect transforming the (N) corrected perceived locations and the (N) corrected perceived orientations into a corrected ocular motor functioning map illustrating the torsional component of an ocular motility disease.

* * * * *